United States Patent [19]

Orly et al.

[11] Patent Number: 5,658,593
[45] Date of Patent: Aug. 19, 1997

[54] INJECTABLE COMPOSITIONS CONTAINING COLLAGEN MICROCAPSULES

[75] Inventors: Isabelle Orly, Lyons; Alain Huc, Ste Foy les Lyon, both of France

[73] Assignee: Coletica, Lyons, France

[21] Appl. No.: 594,479

[22] Filed: Jan. 31, 1996

Related U.S. Application Data

[63] Continuation of Ser. No. 256,589, Jul. 28, 1994, abandoned.

[30] Foreign Application Priority Data

Jan. 16, 1992 [FR] France .................................. 92 00411

[51] Int. Cl.⁶ .................................................. A61K 9/50
[52] U.S. Cl. ........................ 424/499; 424/422; 424/426; 424/489; 428/402.24
[58] Field of Search ................................. 424/422–426, 424/489–499; 428/402.24

[56] References Cited

U.S. PATENT DOCUMENTS

| | | | |
|---|---|---|---|
| 4,178,152 | 12/1979 | Nunogaki | 23/230 B |
| 4,619,913 | 10/1986 | Luck | 514/2 |
| 4,851,220 | 7/1989 | Yim | 424/85.7 |
| 5,001,169 | 3/1991 | Nathan | 523/113 |
| 5,137,875 | 8/1992 | Tsunenaga | 514/21 |
| 5,244,672 | 9/1993 | Huc | 424/450 |
| 5,246,698 | 9/1993 | Leshchiner | 424/78.08 |
| 5,306,500 | 4/1994 | Rhee | 424/422 |

FOREIGN PATENT DOCUMENTS

| | | |
|---|---|---|
| 0196197 | 10/1986 | European Pat. Off. . |
| 0230647 | 8/1987 | European Pat. Off. . |
| 0381543 | 8/1990 | European Pat. Off. . |
| 0397542 | 11/1990 | European Pat. Off. . |

*Primary Examiner*—Gollamudi S. Kishore
*Attorney, Agent, or Firm*—Foley & Lardner

[57] ABSTRACT

A collagen-based composition including microcapsules of atelocollagen or of a mixture of atelocollagen and a polysaccharide, particularly glycosaminoglycan, suspended in a viscous biocompatible carrier solution. Together, the microcapsules and the viscous carrier solution preferably have a viscosity such that the composition may be injected, in particular as a continuous thread from a needle. Said composition is readily injectable and may be used as a soft or bony tissues filling material for, or as a system for the controlled delivery and release of biologically, cosmetically or pharmaceutically active substances.

58 Claims, No Drawings

INJECTABLE COMPOSITIONS CONTAINING COLLAGEN MICROCAPSULES

This application is a continuation of application Ser. No. 08/256,589, filed Jul. 28, 1994 now abandoned which is a 371 of PCT/FR 93/00035, filed Jan. 14, 1993.

FIELD OF THE INVENTION

The present invention essentially relates to injectable compositions containing collagen-based microcapsules in suspension, to their biomedical use and to pharmaceutical compositions.

The invention relates more precisely to the preparation of an injectable carrier which makes it possible to fill in losses of substance or to conveniently introduce active substances in the system of live beings, in particular humans.

PRIOR ART

A large number of investigations have been conducted to develop filling-in materials. Suitable ways of filling in soft tissues are:

- injections of silicones, gelatin, autologous and heterologous collagen
- implantation of threads (catgut, Gore-tex, collagen). It has become clear today that the material giving the best performance, from the point of view of biocompatibility and stability in vitro is heterologous (of bovine origin) collagen (injectable and threads).

The most common applications of the materials for filling-up soft tissues relate essentially to the treatment of skin depressions and losses of facial substances due to age (wrinkles), or to other causes (diseases, traumatisms, surgical operations, . . . ) and which cause scars, emaciations, irregularities, etc . . .

In some of these cases, the use of crosslinked collagen threads such as described in document No. 91 04518 filed by BIOETICA is especially indicated on account of the high properties of biocompatibility, stability in vitro and filling-up power of this material.

Nevertheless, although the use of such threads is quite suitable for filling-up deep wrinkles, it has been found to be less adapted to other situations (such as for example, superficial wrinkles, non-furrowlike skin defects). In those cases, it is necessary to resort to an injectable form.

Also, besides plastic surgery, there are medical fields (such as otorhinolaryngology, urology, orthopedics, . . . ) for which the nature of the fillings to be performed and/or the accessibility of the implanting sites necessarily require the use of an injectable form.

The most recent among the existing inventions are described in documents EP 83868 A1 and EP 89145 A2 filed by the company COLLAGEN CORPORATION, EP 132979 A2 filed by the company KOKEN CO. LTD. and U.S. Pat. No. 3,949,073.

The existing injectable collagens are collagenic solutions. In most cases the implant should be able to be injected with fine needles (generally having a diameter of 0.3 to 0.5 mm). To meet this requirement, the solutions have to be relatively fluid hence of low concentration (2 to 6.5%). Such limitation raises the problem of biodegradability and of stability in time of such implants, the quantities of active substances administered being relatively low.

For reasons of solubility and biocompatibility, the collagen used is an atelocollagen, namely a collagen from which the end regions of non-helical structure called telopeptides have been eliminated. Said telopeptides are indeed where cross link-type intra- and inter-molecular bonds occur, which bonds make the collagen non-soluble. Moreover, the telopeptides carry the principal antigenic determinants of collagen. In the existing products, atelocollagen is obtained by protease treatment with pepsin which preferentially attacks the telopeptides without destroying the helical structure. Pepsin, however, has the disadvantage of settling very firmly on its substrate and is therefore difficult to eliminate. As it happens, it is a very strongly antigenic molecule of which the presence, even in small quantity, risks to alter the biocompatibility of the product thus obtained.

To ensure its filling-up function, the implant should, after injection, retain a certain volume and it should not spread too much through the surrounding tissues. Thus, it constitutes a kind of matrix which, being maintained long enough, settles in the host tissues and enables a restoration of the treated area. In the existing products, such characteristic is met by using atelocollagen solutions which precipitate at body temperature, thus leading to the formation of fibers which remain at the injection site whereas the excipient is progressively resorbed (see U.S. Pat. No. 3,949,073).

The result is that before being injected, the product has to be kept at low temperature (below 10° C.) so that it can retain its fluidity, which property is necessary for it to be administered by injection. Consequently, the injectable collagen based on this principle require particular precautions of preservation which complicate the use thereof.

The major limitation of the prior injectable collagens reside in their resorbability "in vivo".

Indeed, the degradation of collagen is a normal biological process which forms part of the metabolism of the connective tissues. This process involves a number of enzymes, in particular collagenases which are responsible for the initial attack of collagen. The biodegradability of collagen raises a particularly important problem. Indeed, the filling-up of depressions and of losses of substance should be a permanent treatment or in any case a reasonably durable treatment which hardly needs a rapid resorption of the implant.

Different physical and chemical treatments exist, which treatments are able to reduce resorbability by increasing the number of crosslinking bonds between the molecules of collagen. Glutaraldehyde is the most widely used crosslinking agent (as described in EP-A-0 089 145).

It is particularly efficient but has a major disadvantage which is to be polymerized when in solution. Accordingly, materials which are crosslinked with this agent release, after a time, glutaraldehyde monomers which are cytotoxic beyond 10-25 ppm. Therefore, the injectable collagens prepared according to this principle (Patent EP 89 145 A2) are generally less degradable than the non-crosslinked implants (average stability between 1 and 2 years instead of 6 months to one year, as regards filling-up of wrinkles). On the other hand, they can cause more frequent adverse reactions which raises a certain amount of suspicions and reduces the uses.

SUMMARY OF THE INVENTION

The main object of the present invention is to provide a solution for preparing an injectable material which is easy to inject even with a fine needle whose diameter is between 0.3 and 0.5 mm, and a high collagen content, in particular at least 7% by weight/volume and preferably as high as about 10%.

Another object of the present invention is to solve the new technical problem indicated above by providing a solution whereby a system is proposed for carrying active substances while allowing the therapeutic optimization of the active molecules, for example by controlled release into the organism, by screening of the tissues or organs concerned, and by protection of the natural substances.

Yet another object of the present invention is to solve the new technical problem indicated above by providing a solution of improved biocompatibility in which the degradation products do not create residues liable to cause undesirable reactions.

A further object of the present invention is to solve the new technical problems indicated above with a solution whereby the degradation rates of the material injected in a live being, in particular a human being, are modulated so as to be able to adjust the life duration of an implant as well as the vehiculated active substance-release kinetics.

The object of the invention is also to provide filling materials whose stability in vivo can be at least equal to that of the collagen materials treated with glutaraldehyde.

All said technical problems have been solved simultaneously, and in a satisfactory, safe, reliable and reproducible manner, usable on an industrial and medical scale, while being inexpensive.

Thus, in a first aspect, the present invention provides a collagen-based composition, which is easy to inject, characterized in that it comprises microcapsules of atelocollagen or of a mixture of atelocollagen with a polysaccharide, in particular a glycosaminoglycan, in suspension in a viscous biocompatible carrier solution. Preferably, the microcapsules together with the viscous carrier solution have, as a whole, a viscosity which permits the injection of said composition, particularly in the form of a continuous thread from a needle.

According to a particular variant of embodiment, the carrier solution comprises at least a protein substance, such as for example atelocollagen and/or a polysaccharide substance.

If the carrier solution contains a protein substance, said substance is advantageously atelocollagen, which may be obtained by enzymatic or chemical means, preferably by chemical treatment notably with sodium hydroxide, the chemical treatment being particularly advantageous in that it prevents any residual presence of enzyme as it happens if an enzymatic treatment is used, the enzyme being usually pepsin, which increases the biocompatibility of the material. If the atelocollagen is obtained by enzymatic treatment, notably with pepsin, or by chemical treatment, notably with sodium hydroxide, it is possible to modulate the degree of decrosslinking of collagen, hence the viscosity of the carrier material.

According to another particular variant of embodiment, the polysaccharide substance is used, optionally mixed with the protein substance in the carrier material, and it is selected from the group consisting of a glycosaminoglycan, an alginate, a dextran, a cellulose or a cellulose derivative, xanthan gum, gum arabic, and mixtures thereof.

Thus, according to an advantageous variant of embodiment, the atelocollagen in the microcapsules is decrosslinked with a decrosslinking rate adapted to the proposed application.

The polysaccharide which can be used in mixture with atelocollagen for the preparation of said microcapsules, is in particular a glycosaminoglycan selected among the group consisting of the structural glycosaminoglycans selected among chondroitine-4-sulfate, chondroitine-6-sulfate, dermatan-sulfate, heparan-sulfate, keratan-sulfate, as well as heparin and its derivatives, particularly the heparins of low molecular weight having a molecular weight comprised between about 2,000 and about 10,000; and a polyholoside, and in particular dextran.

The process for preparing the microcapsules is based on that described in Applicant's prior patent FR-A-2 642 329 (corresponding to U.S. Pat. No. 5,395,620) incorporated herein by way of reference.

Advantageously, the proportion of polysaccharide with respect to atelocollagen is comprised between 10 and 70%, and better still between 15 and 50% by weight.

The preparation of the microcapsules consists in crosslinking the atelocollagen and optionally the polysaccharides by interfacial crosslinking, this is done by producing an emulsion of the solution of atelocollagen and polysaccharides as phase dispersed in a hydrophobic liquid forming the continuous phase, in which the atelocollagen and/or the polysaccharides are essentially non-soluble.

For the crosslinking, a crosslinking agent is added to the emulsion of the solution of atelocollagen and optionally of the polysaccharides, said crosslinking agent comprising reactant groups capable of reacting with the acylable groups of the atelocollagen and of polysaccharides so as to cause an interfacial crosslinking reaction. A preferred crosslinking agent is an acid dichloride or an acid anhydride or a di- or polybasic carboxylic acid. Other preferred crosslinking agents are, terephtaloyl chloride, phtalic acid chloride, sebacic acid chloride, succinic acid chloride, the chloride of a tricarboxylic acid such as citric acid or an anhydride of an acid such as succinic anhydride.

As hydrophobic liquid, in which the atelocollagen and/or polysaccharides are non-soluble, it is preferred to use fatty acid esters such as selected among those which can normally be administered by parenteral route, such as triglycerides, ethyl oleate; or which have no toxic properties, such as isopropyl myristate, 2-hexyl ethyl cocoate.

The concentration of polysaccharides in the polysaccharide solution is advantageously between 0.5 and 4%, and better still between 0.5 and 2%, and even preferred around 1%.

The atelocollagen solution for the preparation of the microcapsules is an aqueous solution of atelocollagen having a concentration comprised between 0.5 and 2% by weight.

For preparing the microcapsules, the atelocollagen may have been obtained by enzymatic digestion of collagen, notably using pepsin, or else by chemical treatment using sodium hydroxide.

For the actual process for preparing the microcapsules, reference will be made to document FR-A-2 642 329 (corresponding to U.S. Pat. No. 5,395,620), incorporated herein by way of reference, and in particular to Examples 1 to 6.

According to an advantageous embodiment, the size of the microcapsules is less than or equal to 500 μm. In some cases, the size of the microcapsules is less than 250 μm and can even be comprised between 20 and 50 μm, in particular in the case where the composition is supposed to be injected with a fine needle having a diameter comprised between 0.3 and 0.5 mm.

According to a particular variant, the relative proportion of the microcapsules with respect to the viscous biocompatible carrier solution is comprised between 0.5–15/99.5–85 by weight/volume.

According to a particularly advantageous embodiment, the microcapsules contain at least an active substance which is, either encapsulated within, or in the mass of the walls of the microcapsules, or grafted on the internal and/or external surface. Said active substance may be biologically, cosmetically or pharmaceutically active. By biologically active substance is meant a substance having a biological effect on the system which is not necessarily cosmetic or therapeutical. A currently preferred active substance is hydroxyapatite, particularly in particle form, for example of size equal to about 50 μm.

In a second aspect, the present invention also provides a use of said composition as carrier agent of biologically, cosmetically or pharmaceutically active substance.

The present invention further relates to a pharmaceutical composition, characterized in that it contains a collagen-based composition which is readily injectable as defined hereinabove.

The invention finally relates to an implant, characterized in that it is prepared from an injectable composition as defined hereinabove.

Moreover, the invention further relates to special embodiments of compositions. A preferred special embodiment is an embodiment in which the microcapsules are based on atelocollagen optionally mixed with a glycosaminoglycan such as chondroitine-4-sulfate, said microcapsules containing granules of hydroxyapatite in suspension in a viscous biocompatible carrier solution of a gel of atelocollagen optionally mixed with a glycosaminoglycan, in particular chondroitine-4-sulfate. When the granules of hydroxyapatite have a dimension of about 50 μm, the microcapsules have a dimension of about 200 μm.

According to a particularly advantageous embodiment, the viscous biocompatible carrier solution is adapted to the physiological conditions of pH and of osmotic pressure, having preferably a pH comprised between 6.8 and 7.5 and an osmotic pressure comprised between 260 and 320 mOsm/1 $H_2O$. Such a pH and osmolarity of the carrier solution can be obtained by adjusting with a phosphate buffer containing for example a mixture of phosphates, of mono- and disodic sodium and/or potassium, or of a mixture of phosphate buffer and sodium chloride for completing the solution carrying the suspension of microcapsules.

Owing to the nature of the constituents of the microcapsules, atelocollagen optionally mixed with polysaccharides, the microcapsules are soft, deformable, so that when in suspension in the viscous biocompatible carrier solution according to the invention, the composition has, as a whole, flowing properties such that it is possible to easily inject, with a needle having a diameter of 0.3 to 0.5 mm, a material containing as much as 10% collagen by weight/volume. This possibility represents an increase of 35% with respect to the most concentrated prior products (6.5%).

Thus, the compositions according to the invention are particularly suitable to be used as filling-in materials, either for filling-in soft tissues, or as bone fillings for bone reconstruction. In such applications, it is obvious that any increase of the active substance concentration causes a de facto increase of the life of the implant and of the efficiency of the filling.

The composition according to the invention thus combines the biological properties of collagen, in its atelocollagen form, with those of any other substances that may be used (polysaccharides crosslinked together with the atelocollagen, active substances in solution or in suspension in the spheres, molecules grafted on their surface).

Thus, the compositions according to the invention have a wide range of applications as carrier systems for active substances. This galenic form is particularly advantageous in that it enables, depending on the uses:

therapeutic optimization of the active molecules by controlled release into the system, screening of the target tissues or organs, protection of the natural parts;

access through percutaneous route to areas which are normally only accessible by surgical route (for example, the bone areas), thus limiting the traumatism suffered by the patient and the hospitalization time and costs.

Obviously, it is also possible to envisage a number of applications in which the function of filling-in is advantageously combined with the use of a particularly advantageous galenic form.

The composition according to the invention is particularly adapted to the use as a carrier insofar as its degradation does not create residues liable to cause undesirable reactions. This constitutes a major advantage over certain synthetic polymers of the prior art.

Degradation of the microcapsules can be modulated within very wide limits, on the one hand by a variable degree of decrosslinking of the atelocollagen by chemical or enzymatic means; and on the other hand, by adjusting the rate of interfacial crosslinking. It is thus possible to adjust the speed of resorbability from a fast speed to a speed higher than that obtained with materials crosslinked with glutaraldehyde, while avoiding the disadvantages linked to the toxicity of that agent.

Thus, the range of application of the compositions according to the invention is multiplied, by relying on the duration of the composition, particularly in implant form, whether it is intended to stay the longest possible time in the implanting area or to be resorbed and replaced more or less rapidly by the host tissues; and the kinetics of the release of the active substance.

It is therefore understandable that the present invention provides a technical solution which has definite technical advantages over the prior art.

Other objects, characteristics and advantages of the invention will be more clearly understood from the explanatory description given with reference to several examples of embodiment of the present invention and just by way of illustration and which could not possibly limit the scope of the invention in any way. However, the examples form an integral part of the invention and the man skilled in the art will, on reading them, appreciate the new general characteristics resulting therefrom.

In the examples, all the percentages are given by weight, except where otherwise stated.

EXAMPLE 1

Suspension of atelocollagen microcapsules of 20 to 50 μm in an atelocollagen gel.

This suspension constitutes a product intended to ensure a filling-in function, particularly for soft tissues.
a) Preparation of atelocollagen by treatment with pepsin Calf's skin from an animal just slaughtered is subjected to a chemical depilatory treatment in a bath containing 3% sodium sulfide and 4% lime, the proportion being 1200 g of skin for 200 ml of solution. The dermis is then isolated from the rest of the skin by a ripping operation with a rotating band saw.

The obtained tissue is ground and extruded through a screen having 4 mm holes.

The ground material is dispersed in a solution of acetic acid 0.5M containing pepsin in the proportion of 1 g enzyme for 10 g of dry collagen, the pH of the mixture being adjusted if necessary to obtain a pH of between 2 and 3. After stirring, the mixture is left to incubate for 36 hours at 10° C. After filtration, the collagen is precipitated by the addition of NaCl 0.7M. After stirring and incubation (4 hours), the precipitated fibers are recovered by centrifuging (14 000 rpm). The supernatant is eliminated and the pepsin is inactivated by dispersion of the residue in a Tris buffer 0.05M–NaCl 0.15M of which the pH is adjusted, after dispersion of the fibers, to 8.5. After 3 days' incubation at 10° C., the dispersion is dialyzed against deionized and sterile water using dialysis membranes, preferably formed by tubings of which the cutting threshold is between 6,000 and 8,000 daltons.

b) Preparation of the ateloeollagen solution in a buffer medium of pH 8-8.2

The atelocollagen coming from the dialysis tubings is diluted with a solution of sodium bicarbonate, of volume and concentration such that the final concentrations are as follows:

The atelocollagen 1% anhydrous bicarbonate of sodium 4%

It is checked that the pH of the obtained solution is definitely comprised between 8 and 8.2. 1 kg of such solution is prepared.

c) Preparation of the crosslinking agent 100 g of terephtaloyl chloride are added to 4 l of a hydrophobic solvent, preferably fatty acid esters selected among those which can normally be administered by the parenteral route (such as triglycerides, ethyl oleate), or among those which have no toxic properties (such as isopropyl myristate, ethyl-2-hexyl cocoate). The mixture is stirred mechanically.

d) Emulsification 3 l of the hydrophobic solvent selected in accordance with the aforecited criteria are introduced into a container. The previously prepared buffered atelocollagen solution is added under stirring to the Ultra Turax® turning at 7,200 rpm.

e) Crosslinking

The crosslinking agent solution is added to the resulting emulsion. Stirring is kept up for 30 mins.

Microcapsules are thus obtained.

f) Washes

Three washes are carried out with 10 l of hydrophobic solvent and the microcapsules are collected by decantation with a Robatel decanter turning at 1,000 rpm.

Five to eight washes in ethanol (a total of 15 to 20 l) are performed in the same way, followed by three to five washes in deionized and sterile water.

g) Lyophilization

A lyophilization of the washed product containing the microcapsules is conducted in the conventional way.

h) Sterilization

After packing the dry spheres in a sealed package, the microcapsules are sterilized by being exposed to gamma rays (25 kGy).

i) Preparation of the suspension medium

The atelocollagen is obtained by treatment with soda in the conditions explained hereafter.

After depilation, ripping and grinding of the skins such as described in a), the ground material undergoes two washes with a phosphate buffer of pH 7.8 (21.7 g/l of $NA_2HPO_4$ and 0.78 g/l of $KH_2PO_4$) and then two washes in deionized and sterile water.

The ground material is then placed for eight days in contact with a solution of soda in the proportion of 1 kg of ground material for 4 l of solution of concentration such that the final quantity of soda is 8% (w/v). After this treatment, the atelocollagen is precipitated by the addition of hydrochloric acid concentrated reaching a pH of between 2 and 2.5. The resulting suspension is introduced in dialysis tubing (having a cutting threshold of between 6,000 and 8,000 daltons) and dialyzed against deionized and sterile water.

The obtained atelocollagen is then lyophilized, sterilized by gamma rays and placed in solution in sterile conditions. The pH and osmolarity of the solution are adjusted by using a phosphate buffer (mixture of mono- and disodic sodium and/or potassium phosphates) or a mixture of phosphate buffer and sodium chloride so as to obtain a pH comprised between 6.8 and 7.5 and an osmotic pressure comprised between 260 and 320 mOm/l $H_2O$.

Example of composition of the suspension medium:

Atelocollagen 1%

$Na_2HPO_4$ 0.02M

NaCl 0.13M pH 7.3 j) Placing the microcapsules in suspension

The microcapsules are placed in suspension in the atelocollagen suspension medium obtained in step i) in sterile conditions in the proportion of 100 mg of dry spheres per ml of suspension medium. The suspension is stirred so as to obtain a perfectly homogeneous mixture. The pH of the mixture is checked.

k) Preparation of the syringes

The mixture is introduced in sterile conditions, in syringes of 1 ml equipped with a luer-lock type endpiece and needles of diameter between 0.3 and 0.5 mm.

l) Evaluation of the obtained product

* Thermal stability by Programmed Differential Scanning Calorimetry:

The parameters recorded on the microcapsules after lyophilization are as follows:

beginning-of-denaturation temperature: 65° C.

peak-of-denaturation temperature: 72.6° C.

end-of-denaturation temperature: 80° C.

These values are particularly high and are of the same magnitude than with the products obtained by crosslinking with glutaraldehyde for example.

* Evaluation in vivo:

The tests were conducted on Wistar female rats weighing between 180 and 200 g.

The material was implanted on the rats' back, in subcutaneous position. Each implanting site (2 per rat) received about 0.1 ml of the suspension.

The biopsies and histological controls conducted after 1 and 7 days of implantation have shown:

a high filling-in power a perfect biocompatibility a total absence of degradation of the implant.

These results ensure for the implant a particularly high long-term stability.

EXAMPLE 2

Suspension of microcapsules of atelocollalagen and of chondroitin-4-sulfate of about 200 μm containing granules of hydroxyapatite in a gel of atelocollagen and chondroitine-4-sulfate.

In this example, granules of hydroxyapatite (a mineral chemical composition close to the bone mineral and used in bone reconstructions) are incorporated in microcapsules. This system makes it possible to carry the granules of hydroxyapatite and makes them injectable through a trocar. They can thus be implanted in a bone area by percutaneous route.

a) Preparation of the atelocollagen by treatment with soda

This step is performed in the same conditions as those described in Example 1, paragraph i).

b) Preparation of the chondroitine-4-sulfate

Nasal septa from lambs, wherefrom the muscular and adipous tissues have been removed are chopped and ground by extrusion through a screen having 4 mm holes; the ground material is placed for 24 hours at a temperature of 6° C. in a buffer of potassium chloride (11.8 g/l of KCl; 78.8 mg/l of cysteine, 180 mg/l of EDTA) containing 1% of "MERCK" papain. The proportion being of 130 g of ground material for 1 l of buffer.

The supernatant is separated from the residue by continuous centrifuging using a decanter turning at 4.000 rpm. 40 g/l of trichloroacetic acid are then added to the supernatant. The precipitate is eliminated by continuous centrifuging according to the preceding technique. The supernatant is neutralized with pellets of soda. The mixture is then dialyzed against deionized and sterile water using tubing having a curing threshold between 6 and 8,000 daltons. The dialyzed solution is liophylized. The chondroitine-4-sulfate is obtained in dry state.

c) Preparation of the solution of ateloeollagen and of chondroitin-4-sulfate in a buffer medium of pH 8.9

The atelocollagen in fiber form coming from the dialysis tubing is diluted with a solution containing chondroitin-4-sulfate and sodium carbonate of volume and concentration such that the final concentrations are as follows:

Atelocollagen: 1.6%

Chondroitin-4-sulfate: 0.6%

Anhydrous sodium carbonate: 4.8%

The pH of the mixture is adjusted to 8.9 with concentrated hydrochloric acid. 1 kg of this solution is prepared.

d) Incorporation of hydroxyapatite

The hydroxyapatite is incorporated in the form of spherical granules of about 50 μm diameter to the preparation described hereinabove, in the proportion of 5% (w/v).

e) Preparation of the crosslinking agent 180 g of terephtaloyl chloride are added to 4 l of isopropyl myristate. The mixture is stirred mechanically.

f) Emulsification 150 ml of Span 85 (ICI Company) are mixed with 3 l of isopropyl myristate. The collagen solution containing hydroxyapatite is poured into the mechanically stirred mixture. The whole is stirred for a few minutes in order to obtain the emulsion.

g) Crosslinking

The crosslinking agent solution is added to the resulting emulsion. Stirring is kept up for 30 minutes.

The microcapsules containing the granules of hydroxyapatite are thus obtained.

h) Washes

The microcapsules are washed in the same conditions as those described in Example 1.

i) Preparation of the suspension medium

The atelocollagen coming from the dialysis tubing is diluted with a solution of chondroitin-4-sulfate of volume and concentration such that the final concentrations are as follows:

Atelocollagen 0.8% pl Chondroitin-4-sulfate 0.2% j) Placing the microcapsules in suspension

The microcapsules are placed in suspension in the medium described hereinabove in proportions such that in the final mixture 90% of the mixture composed of atelocollagen and chondroitin-4-sulfate come from the microcapsules and 10% come from the suspension medium.

A composition according to the invention is thus obtained, which composition can be used as is or it can be treated as described hereunder.

k) Lyophilization

The composition obtained in step j is lyophilized in conventional manner.

l) Sterilization

Same conditions as in Example 1.

m) Rehydration in buffer medium

The lyophilisate is placed in suspension in sterile conditions in the proportion of 500 mg of lyophilisate per ml of phosphate buffer 0.1M. The pH of the phosphate buffer is fixed so that the pH of the mixture is between 7 and 7.3.

n) Preparation of the syringes

The mixture is introduced, in sterile conditions, in 5 ml syringes equipped with needles of 1.5 mm diameter.

We claim:

1. A readily injectable collagen-containing composition, comprising microcapsules having an outerwall of a crosslinked collagen component selected from the group consisting of crosslinked atelocollagen and of a crosslinked mixture atelocollagen with a polysaccharide, said microcapsules being in suspension in a viscous biocompatible carrier solution which comprises a viscosity from promoting substance selected from the group consisting of a protein, a polysaccharide and mixtures thereof, said viscous solution containing in suspension said microcapsules having an overall viscosity providing injectability of said composition with a needle having a diameter ranging between 0.3 and 1.5 mm, and said microcapsules provide an atelocollagen content of at least 7% weight/volume.

2. The composition according to claim 1, wherein said microcapsules provide an atelocollagen content of at least 10% weight/volume.

3. The composition of claim 2, wherein said protein is selected from the group consisting of atelocollagen and a mixture of atelocollagen and a polysaccharide.

4. The composition of claim 1, wherein said atelocollagen is obtained by chemical treatment which converts collagen to atelocollagen.

5. The composition of claim 4, wherein said chemical treatment comprises a treatment with a basic aqueous solution.

6. The composition of claim 1, wherein the polysaccharide is selected from the group consisting of a glycosaminoglycan, an alginate, a dextran, a cellulose, a xanthan gum, an arabic gum, and the mixtures thereof.

7. The composition of claim 1, wherein said polysaccharide is a glycosaminoglycan selected from the group consisting of chondroitin-4-sulfate, chondroitin-6-sulfate, dermatan-sulfate, heparan-sulfate, keratan-sulfate.

8. The composition of claim 1, wherein said polysaccharide is selected from the group consisting of heparin and low molecular weight heparins having a molecular weight ranging between about 2,000 and about 10,000.

9. The composition of claim 1, wherein the relative proportion by weight/volume of the microcapsules with respect to the carrier solution ranges between 0.5 and 15% by weight of microcapsules with respect to the volume of the carrier solution.

10. The composition of claim 1, wherein the proportion by weight of the polysaccharide in the microcapsules with respect to atelocollagen ranges between 10 and 70%.

11. The composition according to claim 10, wherein said microcapsules contain a substance which is selected from the group consisting of a cosmetically active substance and a pharmaceutically active substance.

12. The composition of claim 1, wherein the size of the microcapsule is less than about 500 μm.

13. The composition of claim 1, wherein said microcapsules contain granules of hydroxyapatite.

14. The composition of claim 1, wherein the carrier solution comprises a gel of atelocollagen.

15. The composition of claim 14, wherein said gel of atelocollagen further comprises a glycosaminoglycan.

16. The composition of claim 15, wherein said glycosaminoglycan is chondroitin-4-sulfate.

17. The composition of claim 13, wherein the atelocollagen content in said composition is about 10% by weight/volume.

18. The composition of claim 1, wherein the degradation of microcapsules is controlled by adjusting the crosslinking rate of atelocollagen.

19. The composition of claim 1, wherein the degradation of microcapsules is controlled by adjusting the decrosslinking rate of atelocollagen.

20. The composition of claim 1, wherein said viscous biocompatible carrier solution is adapted to the physiological conditions of pH and osmotic pressure.

21. The composition of claim 1, wherein said viscous biocompatible carrier solution has a pH ranging between 6.8 and 7.5 and an osmotic pressure ranging between 260 and 320 mOsm/liter water.

22. The composition of claim 21, wherein the pH is adjusted with a phosphate buffer.

23. The composition of claim 22, wherein said phosphate buffer further comprises sodium chloride.

24. The composition of claim 1, which is a pharmaceutical composition.

25. The composition of claim 1, in a form selected from the group consisting of an implant, a filling-in material, a filling-in material for soft tissues and a filling-in material for bone reconstruction.

26. The composition of claim 1, wherein said microcapsules are lyophilized microcapsules which have been rehydrated.

27. The composition of claim 1, wherein said viscous biocompatible carrier solution is a lyophilized biocompatible carrier which has been rehydrated.

28. The composition of claim 1, wherein said microcapsules are lyophilized microcapsules which have been rehydrated, and said viscous carrier solution is a lyophilized biocompatible carrier which has been rehydrated.

29. The composition according to claim 1, wherein 10% of the total amount of atelocollagen in said composition comes from said viscous biocompatible carrier solution, and the remainder of the atelocollagen comes from said microcapsules.

30. The composition of claim 3, wherein the biocompatible carrier solution and the microcapsules are produced from the same atelocollagen containing solution.

31. A method of injecting a filling material in predetermined areas of a living animal, comprising injecting in said predetermined areas, a filling material comprising microcapsules having an outerwall of a crosslinked collagen component selected from the group consisting of crosslinked atelocollagen and a cross mixture of atelocollagen with a polysaccharide, said microcapsules being in suspension in a viscous biocompatible carrier solution which comprises a viscosity promoting substance selected from the group consisting of a protein, a polysaccharide and mixtures thereof, said viscous solution containing in suspension said microcapsules having an overall viscosity providing injectability with a needle having a diameter ranging between 0.3 and 1.5 mm, and said microcapsules provide an atelocollagen content of at least 7% weight/volume.

32. The method of claim 31, wherein said protein is selected from the group consisting of atelocollagen and a mixture of atelocollagen and polysaccharide.

33. The method of claim 31, wherein said atelocollagen is obtained by chemical treatment which converts collagen to atelocollagen.

34. The method of claim 33, wherein said chemical treatment comprising a treatment with a basic aqueous solution.

35. The method of claim 31, wherein the polysaccharide is selected from the group consisting of a glycosaminoglycan, an alginate, a dextran, a cellulose, a xanthan gum, an arabic gum, and the mixture thereof.

36. The method of claim 31, wherein said polysaccharide is a glycosaminoglycan selected from the group consisting of chondroitin-r-sulfate, chondroitin-6-sulfate, dermatan-sulfate, heparan-sulfate, keratan-sulfate.

37. The method of claim 31, wherein said polysaccharide is selected from the group consisting of heparin and low molecular weight heparins having a molecular weight ranging between about 2,000 and 10,000.

38. The method of claim 31, wherein the relative proportion by weight/volume of the microcapsules with respect to the carrier solution ranges between 0.5 and 15% by weight of microcapsules with respect to the volume of the carrier solution.

39. The method of claim 31, wherein the preparation by weight of the polysaccharide in the microcapsule with respect to atelocollagen ranges between 10 and 70%.

40. The method according to claim 31, wherein said microcapsules contain a substance which is selected from the group consisting of a cosmetically active substance, a biologically active substance and a pharmaceutically active substance.

41. The method of claim 31, wherein the size of the microcapsule is less than about 500 μm.

42. The method of claim 31, wherein said microcapsules contain granules of hydroxyapatite.

43. The method of claim 31, wherein the carrier solution comprises a gel of atelocollagen.

44. The method of claim 43, wherein said gel of atelocollagen further comprises a glycosaminoglycan.

45. The method of claim 44, wherein said glycosaminoglycan is chondroitin-4-sulfate.

46. The method of claim 31, wherein said microcapsules provide an atelocollagen content of at least 10% weight/volume.

47. The method of claim 31, wherein the degradation of microcapsules is controlled by adjusting the crosslinking rate of atelocollagen.

48. The method of claim 31, wherein the degradation of microcapsules is controlled by adjusting the decrosslinking rate of atelocollagen.

49. The method of claim 31, wherein said viscous biocompatible carrier solution is adapted to the physiological conditions of pH and osmotic pressure.

50. The method of claim 31, wherein said viscous biocompatible carrier solution has a pH ranging between 6.8 and 7.5 and an osmotic pressure ranging between 260 and 320 mOsm/liter water.

51. The method of claim 50, wherein the pH is adjusted with a phosphate buffer.

52. The method of claim 51, wherein said phosphate buffer further comprises sodium chloride.

53. The method of claim 31, which comprises injecting said filling material to yield an implant.

54. The method of claim 31, which performs bone reconstruction.

55. The method of claim 31, wherein the living being is a human being.

56. The method of claim 31, wherein said microcapsules are lyophilized microcapsules which have been rehydrated.

57. The method of claim 31, wherein said viscous biocompatible carrier solution is a lyophilized biocompatible carrier which has been rehydrated.

58. The method of claim 31, wherein 10% of the total amount of atelocollagen of said filling material comes from said viscous biocompatible carrier solution, and the remainder of the atelocollagen comes from said microcapsules.

* * * * *